US010023698B2

(12) United States Patent
Gorodisher et al.

(10) Patent No.: US 10,023,698 B2
(45) Date of Patent: Jul. 17, 2018

(54) CURABLE BENZOXAZINE COMPOSITIONS WITH IMPROVED THERMAL STABILITY

(71) Applicant: 3M INNOVATIVE PROPERTIES COMPANY, St. Paul, MN (US)

(72) Inventors: Ilya Gorodisher, Stillwater, MN (US); Gregory P. Sorenson, Maplewood, MN (US); Mark McCormick, St. Paul, MN (US); Katri M. Huikko, Cottage Grove, MN (US); Robert J. Webb, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/515,162

(22) PCT Filed: Dec. 8, 2015

(86) PCT No.: PCT/US2015/064366
§ 371 (c)(1),
(2) Date: Mar. 29, 2017

(87) PCT Pub. No.: WO2016/099988
PCT Pub. Date: Jun. 23, 2016

(65) Prior Publication Data
US 2017/0283558 A1 Oct. 5, 2017

Related U.S. Application Data

(60) Provisional application No. 62/093,508, filed on Dec. 18, 2014, provisional application No. 62/134,210, filed on Mar. 17, 2015.

(51) Int. Cl.
C07D 265/16 (2006.01)
C08G 73/02 (2006.01)

(52) U.S. Cl.
CPC ....... C08G 73/0233 (2013.01); C07D 265/16 (2013.01)

(58) Field of Classification Search
USPC ........................................................ 528/210
See application file for complete search history.

(56) References Cited

U.S. PATENT DOCUMENTS

| 3,018,262 | A | 1/1962 | Schroeder |
| 3,298,998 | A | 1/1967 | McConnell |
| 3,496,250 | A | 2/1970 | Czerwinski |
| 4,501,864 | A | 2/1985 | Higginbottom |
| 5,543,516 | A | 8/1996 | Ishida |
| 6,160,079 | A | 12/2000 | Ishida |
| 6,207,786 | B1 | 3/2001 | Ishida |
| 6,376,080 | B1 | 4/2002 | Gallo |
| 7,041,772 | B2 | 5/2006 | Aizawa |
| 7,053,138 | B2 | 5/2006 | Magendie |
| 7,517,925 | B2 | 4/2009 | Dershem |
| 8,389,758 | B2 | 3/2013 | Gorodisher |
| 9,416,302 | B2 * | 8/2016 | Salnikov ............ C08G 73/0233 |
| 2010/0044986 | A1 | 2/2010 | Dannenberg |
| 2013/0140738 | A1 | 6/2013 | Gorodisher |
| 2014/0011052 | A1 | 1/2014 | Gorodisher |
| 2014/0034863 | A1 | 2/2014 | Gilstad |
| 2014/0221601 | A1 | 8/2014 | Gorodisher |
| 2015/0031819 | A1 | 1/2015 | Rungta |
| 2015/0045528 | A1 | 2/2015 | Gorodisher |
| 2016/0229957 | A1 | 8/2016 | Gorodisher |

FOREIGN PATENT DOCUMENTS

| WO | WO 2008-095850 | 8/2008 |
| WO | WO 2014-052255 | 4/2014 |
| WO | WO 2014-105422 | 7/2014 |
| WO | WO 2014-179100 | 11/2014 |
| WO | WO 2015-057414 | 4/2015 |

OTHER PUBLICATIONS

Baqur, "Methylol-functional benzoxazines as precursors for high-performance thermoset polymers: Unique simultaneous addition and condensation polymerization behavior", Journal of Polymer Science Part A: Polymer Chemistry, 2012, vol. 50, No. 11, pp. 2275-2285.
Dunkers, "Reaction of benzoxazine-based phenolic resins with strong and weak carboxylic acids and phenols as catalysts", J. Polym. Sci. Part A. Polym Chem., 1999, vol. 37, No. 13, pp. 1913-1921.
Gamlin, "Mechanism and kinetics of the isothermal thermodegradation of ethylene-propylene-diene (EPDM) elastomers", Polymer Degradation and Stability, 2003, vol. 80, No. 3, pp. 525-531.
Ghosh, "Polybenzoxazine-new high performance thermosetting resins: synthesis and properties", Prog. Polym. Sci., 2007, vol. 32, No. 11, pp. 1344-1391.
Ishida, "$2^{nd}$ International Symposium on Polybenzoxazines", $246^{th}$ ACS National Meeting, Oral session, Sep. 8-12, 2013, 4pages.
Ishida, "Cationic ring-opening polymerization of benzoxazines", Polymer, 1999, vol. 40, No. 16, pp. 4563-4570.
Kimura, "New Thermosetting Resin from Bisphenol A-based Benzoxazine and Bisoxazoline", J. App. Polym. Sci., 1999, vol. 72, No. 12, pp. 1551-58.
Park, "Thermal rearrangement of N-benzylanilinium hexafluoroantimonates", Tetrahedron Letters, Oct. 15, 1999, vol. 40, No. 42, pp. 7485-7488.
Rimdusit, "Development of New Class of Electronic Packaging Materials Based on Ternary Systems of Benzoxazine, Epoxy, and Phenolic Resins", Polymer, 2000, vol. 41, No. 22, pp. 7941-7949.
International Search report for PCT International Application No. PCT/US2015/064366 dated Mar. 3, 2016, 5 pages.

* cited by examiner

*Primary Examiner* — Terressa Boykin
(74) *Attorney, Agent, or Firm* — Kent S. Kokko (57) ABSTRACT

A curable benzoxazine composition is described wherein the benzoxazine is derived from an aryl amine having a b.p.>200° C. The curable compositions are more thermally stable and have reduced weight loss and by-products upon cure.

23 Claims, 2 Drawing Sheets

CURABLE BENZOXAZINE COMPOSITIONS WITH IMPROVED THERMAL STABILITY

CROSS REFERENCE TO RELATED APPLICATIONS

This application is a national stage filing under 35 U.S.C. 371 of PCT/US2015/064366, filed Dec. 8, 2015, which claims the benefit of U.S. Application No. 62/093,508, filed Dec. 18, 2014 and U.S. Application No. 62/134,210, filed Mar. 17, 2015, the disclosures of which are incorporated by reference in their entirety herein.

BACKGROUND

Benzoxazines and compositions containing benzoxazine are known (see, for example, U.S. Pat. Nos. 5,543,516 and 6,207,786 to Ishida et al.; S. Rimdusit and H. Ishida, "Development of New Class of Electronic Packaging Materials Based on Ternary Systems of Benzoxazine, Epoxy, and Phenolic Resins", Polymer, 41, 7941-49 (2000); and H. Kimura et al., "New Thermosetting Resin from Bisphenol A-based Benzoxazine and Bisoxazoline", J. App. Polym. Sci., 72, 1551-58 (1999).

U.S. Pat. No. 7,517,925 (Dershem et al.) describes benzoxazine compounds and thermosetting resin compositions prepared therefrom. The compositions are said to be useful for increasing adhesion at interfaces within microelectronic packages and low shrinkage on cure and low coefficient of thermal expansion (CTE).

U.S. Pat. No. 7,053,138 (Magendie et al.) describes compositions comprising benzoxazines and thermoplastic or thermoset resins in the manufacture of prepregs and laminates. The compositions are said to yield flame-proofed laminating resins that have high glass transition temperatures.

U.S. Pat. No. 6,376,080 (Gallo) describes a method of preparing a polybenzoxazine which includes heating a molding composition including a benzoxazine and a heterocyclic dicarboxylic acid to a temperature sufficient to cure the molding composition, thereby forming the polybenzoxazine. The compositions are said to have near-zero volume change after post cure.

U.S. Pat. No. 6,207,786 (Ishida et al.) states that the polymerization of benzoxazine monomers to a polymer is believed to be an ionic ring opening polymerization which converts the oxazine ring to another structure, e.g. linear polymer or larger heterocyclic rings. It is thought that a chain transfer step(s) limits the molecular weight of the resulting polymer and causes some branching. FTIR (Fourier transform infrared) analysis is often used to monitor the conversion of the oxazine rings to polymers to provide an estimate of the rate of polymerization at different temperatures. NMR (nuclear magnetic resonance) spectroscopy can also be used to monitor conversion of benzoxazine monomers to polymer.

Epoxy adhesives have been widely used in structural adhesive applications and satisfy many demanding industrial applications. However epoxies have many noted deficiencies that limit their use including limited high temperature stability, high moisture uptake, shrinkage, and a large exotherm on polymerization.

Polybenzoxazines have been proposed to overcome many of the limitations on epoxies. They have lower exotherms on curing, less shrinkage, have higher thermal stability, low byproducts and may be readily prepared from benzoxazines, which in turn, are readily prepared from an amine, formaldehyde and a phenol in high yields. However, for many applications, the amount of byproducts produced in the curing limits their use. Efforts continue to find curable benzoxazines having improved thermal stability

SUMMARY

The present disclosure is directed to a curable composition comprising a benzoxazine compound derived from an aryl amine having a b.p.>200° C. In some embodiments the benzoxazine is further derived from a phenol having a b.p.>200° C. The curable composition may be cured to produce cured compositions useful in coating, sealants, adhesive and many other applications. The present disclosure further provides a curable composition comprising a benzoxazine compound, which when cured, is useful in high temperature structural adhesive applications. The present disclosure further provides a method of preparing a polybenzoxazine comprising heating the curable composition at a temperature, and for a time sufficient, to effect polymerization.

In one embodiment, the present disclosure provides a polymerizable composition including: a benzoxazine; and a film-forming material, a co-catalyst, a curative, or a combination thereof. In certain embodiments, a polymerizable composition can further include a toughener (i.e., toughening agent), an epoxy resin, a reactive diluent, or combinations thereof.

The present disclosure overcomes many of the deficiencies noted for the polymerization of polybenzoxazines including better thermal stability and fewer byproducts on curing than those derived from low boiling amines.

In some embodiments, the product polybenzoxazines are flexible solids having good thermal stability, and are useful for many industrial applications.

Applicant's experimental results indicate that during the ring opening of benzoxazines by a nucleophilic agent, a methylene exchange appears to take place wherein benzoxazine loses the oxazine methylenes to the nucleophile. In the process, the nucleophilic agent forms its own Mannich structures, HO—$CH_2$-Nu and HO—$CH_2$-Nu-$CH_2$—OH even with limited available water. The reaction also liberates the secondary and primary amines from the parent benzoxazine tertiary amine. At higher temperatures (T>180° C.) the secondary amine structures (and benzoxazines derived from aromatic amines as well) further undergo benzyl anilinium rearrangement which results in additional liberation of primary amines. Reference may be made to US 2014/034863 (Gorodisher et al), incorporated herein by reference. The benzyl anilinium rearrangement temperature may be determined by DSC.

When curing commercial benzoxazines made from bisphenols, formaldehyde and aniline (such as Araldite MT 35600, Araldite 35700 and the like), the liberated primary and secondary amines are anilines. Those anilinic species can react, covalently bonding into the polymeric network by electrophilic addition with the iminium cation. Competing with the chemical reaction is the physical evaporation of the liberated aniline. During the benzyl anilinium rearrangement, aniline is liberated near its boiling point.

The loss of aniline during the benzoxazine polymerization results in voids and defects affording poor coating and adhesive properties. It also unbalances the perfect amine/phenol/formaldehyde stoichiometry from which the benzoxazine molecule is derived, reducing the network toughness and extent of hydrogen bonding.

As result of the selection of aromatic amines having boiling points >200° C., the evaporative losses of the amines are reduced, improving the thermal stability and reducing defects in the resulting benzoxazine coatings.

Preferably the phenol from which the benzoxazine is derived also has a boiling point above the benzyl anilinium rearrangement temperature, e.g. above 200° C.

As used herein, the term "benzoxazine" is inclusive of compounds and polymers having the characteristic benzoxazine ring. In the illustrated benzoxazine group, R is the residue of a mono- or poly-aromatic amine.

I

As used herein "polybenzoxazine" refers to a compound having two or more benzoxazine rings.

As used herein "poly(benzoxazine)" refers to the polymer resulting from ring-opening polymerization of benzoxazine or polybenzoxazine compounds.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, and N both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethyl silyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "residue" is used to define the (hetero)hydrocarbyl portion of a group remaining after removal (or reaction) of the attached functional groups, or the attached groups in a depicted formula. For example, the "residue" of phenylene diamine $H_2N-C_6H_4-NH_2$, is the divalent aryl $-C_6H_4-$.

DETAILED DESCRIPTION

The present disclosure provides curable benzoxazine compounds of the formula:

I where each $R^1$ is an alkyl or H;

each $R^2$ is an H, an alkyl, an aryl or a benzoxazine group;

y is 1 to 4

$R^{aryl}$ is derived from an aryl amine having a boiling point greater than 200° C. and more preferably greater than 210° C.;

N-Bz represents a nitrogen-linked benzoxazine group, and z is 0 to 3, preferably 0 or 1.

It will be apparent that when subscript z is zero the benzoxazine is derived from an aromatic monoamine and when z is 1 the bis-benzoxazine is derived from an aromatic diamine. N-Bz will have the same structure as the fully depicted benzoxazine.

In the preparation of the polybenzoxazine, any benzoxazine compound derived from an aromatic amine having a b.p.>200° C. may be used. Benzoxazines may be prepared by combining a phenolic compound, and aliphatic aldehyde, and a primary aromatic amine (or polyamine) compound, such as an alkyl aniline or napthylamine. U.S. Pat. No. 5,543,516 (Ishida) and U.S. Pat. No. 7,041,772 (Aizawa et al.) hereby incorporated by reference, describe methods of forming benzoxazines. Other suitable reaction schemes to produce mono-, di- and higher-functional benzoxazines are described in N. N. Ghosh et al., *Polybenzoxazine-new high performance thermosetting resins: synthesis and properties*, Prog. Polym. Sci. 32 (2007), pp. 1344-1391.

One suitable method of producing the starting benzoxazine compounds is illustrated by the following reaction scheme:

II wherein
each $R^1$ is H or an alkyl group, and is the residue of an aliphatic aldehyde,
$R^2$ is H, a covalent bond, a phenol or a polyvalent (hetero)hydrocarbyl group, preferably H, a covalent bond or an alkyl group; and
$R^{Aryl}$ is aryl residue of a primary amino compound, $R^{Aryl}(NH_2)_m$ having a b.p.>180° C., where $R^{Aryl}$ is an aryl group, m is 1-4; and x is at least 1.

It will be appreciated that as the $R^2$ group may be part of a polyphenolic compound, said $R^2$ group may bond to another benzoxazine ring as illustrated in Formula IV below. Similarly, as the $R^{Aryl}$ may be derived from a polyamine, the $R^{Aryl}$ may also be bonded to another benzoxazine ring as illustrated in Formula I.

In the preparation of the starting benzoxazine, mono- or polyphenolic compounds may be used. The phenolic compound may be further substituted without limitation is desired. For example, the 3, 4, and 5 positions of the phenolic compound may be hydrogen or substituted with other suitable substituents such as alkyl, cycloalkyl, heterocycloalkyl, aryl, heteroaryl, aralkyl, heteroaralkyl, alkoxy, alkoxyalkylene, hydroxyalkyl, hydroxyl, haloalkyl, carboxyl, halo, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl. Desirably at least one of the positions ortho to the hydroxyl group is unsubstituted to facilitate benzoxazine ring formation.

The aryl ring of the phenolic compound may be a phenyl ring as depicted, or may be selected from naphthyl, biphenyl, phenanthryl, and anthracyl. The aryl ring of the phenolic compound may further comprise a heteroaryl ring containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

Examples or mono-functional phenols include phenol; cresol; 2-bromo-4-methylphenol; 2-allyphenol; 4-aminophenol; and the like. Examples of difunctional phenols (polyphenolic compounds) include phenolphthalein; biphenol; 4-4'-methylene-di-phenol; 4-4'-dihydroxybenzophenone; bisphenol-A; 1,8-dihydroxyanthraquinone; 1,6-dihydroxnaphthalene; 2,2'-dihydroxyazobenzene; resorcinol; fluorene bisphenol; and the like. Examples of trifunctional phenols comprise 1,3,5-trihydroxy benzene and the like.

The aldehyde reactants used in preparing the benzoxazine starting materials include formaldehyde; paraformaldehyde; polyoxymethylene; as well as aldehydes having the general formula R'CHO, where $R^1$ is H or an alkyl group, including mixtures of such aldehydes, desirably having from 1 to 12 carbon atoms. The $R^1$ group may be linear or branched, cyclic or acyclic, saturated or unsaturated, or combinations thereof. Other useful aldehydes include crotonaldehyde; acetaldehyde; propionaldehyde; butyraldehyde; and heptaldehyde.

Amino compounds useful in preparing the starting benzoxazine can be substituted or unsubstituted aromatic amines having at least one primary amine group and having a b.p.>200° C. The aryl ring can be substituted with groups such as alkyl, cycloalkyl, heterocycloalkyl, aryl, heteroaryl, aralkyl, or heteroaralkyl.

Amines useful in the preparation of the starting benzoxazine compounds include those of the formula $R^{Aryl}(NH_2)_m$ include aryl monoamines and polyamines. $R^{Aryl}$ is an aryl group that has a valence of m, m is 1 to 4, and is the residue of a mono-, di- or higher aromatic amine having at least one primary amine group.

Examples of useful aromatic amines include alkylated aniline such as o-, m- or p-toluidine, 2,6-dimethyl aniline, 2,5-dimethyl aniline p-bromoaniline, 3,5-dimethyl aniline and 2,4-dimethyl aniline, p-nitroaniline, di-(4-aminophenyl) sulfone, di-(4-aminophenyl)ether, 2, 2-bis(4-aminophenyl) propane, 4,4'-diamino diphenylmethane, 3,3'-dimethyl(4,4'-diaminodiphenyl methane, m- or p-phenylene diamine, m-xylylene diamine, toluene diamine, 4,4'methylene dianiline benzidine, 4,4'-thiodianiline, 4-methoxy-1,3-phenyl-diamine, 2,6-diaminopyridine, and dianisidine.

It will be understood that monoamines will cyclize with the aldehyde and phenolic compound to produce mono-benzoxazine compounds, while di- or higher amines will cyclize to produce di- and poly-benzoxazine compounds: For example, an aryl diamine will produce a di-benzoxazine,

III wherein
each $R^1$ is H or an alkyl group, and is the residue of an aliphatic aldehyde;
$R^2$ is H, a covalent bond, or a polyvalent (hetero)hydrocarbyl group, preferably H, a covalent bond or a divalent alkyl group;
$R^{Aryl}$ is the aryl residue of a primary aryl diamino compound having a b.p.>200° C.

Further, polymeric benzoxazines may be prepared from a polyphenolic compounds, such as bisphenol-A, and a di- or polyamine

IV wherein
each $R^1$ is H or an alkyl group, and is the residue of an aliphatic aldehyde,
$R^2$ is a covalent bond, or a polyvalent (hetero)hydrocarbyl group, preferably a covalent bond or a divalent alkyl group;

$R^4$ is the (hetero)hydrocarbyl residue of a primary amino compound;
$R^{Aryl}$ is the aryl residue of a primary aryl amino compound having a b.p.>180° C.;
z is at least 1, preferably 2 or greater.

If desired an acid catalyst may be used to promote the ring-opening of the benzoxazine to poly(benzoxazine). Lewis and Brönsted acids accelerate the amine cure of benzoxazine adducts as indicated by the lower onset of polymerization temperature and reduced temperature of the peak of the exotherm corresponding to the cure. Suitable acid catalysts include, but are not limited to: strong inorganic acids such as hydrochloric acid, sulfuric acid, phosphoric acid, and the like; and organic acids such as acetic acid, para-toluene sulfonic acid, and oxalic acid.

In some embodiments "super acids" such as pentafluoroantimonic acids may be used, as described in US2010/044986 (Gorodisher et al.), incorporated herein by reference. In some embodiments, latent acids, which thermally generate acids such as tosylates may be used. In some embodiments, acid-forming peroxy catalysts may be sued, as described in WO2014/105422 (Gorodisher et al.)

Acid catalysts may be used in amounts of 2 wt. % or less, preferably 1 wt. % or less, most preferably 0.5 wt. % or less, relative to the amounts of benzoxazine reactants.

In some embodiments the curable benzoxazine composition may comprise a co-catalyst. Suitable co-catalysts include those selected from the group of elemental sulfur, elemental selenium, a sulfide of a Group VA element (e.g., N, P, As, Sb, Bi) of the Periodic Table (referring to the older CAS or American group numbering system), a sulfide of a Group VIA element (e.g., O, S, Se, Te, Po), a selenide of a Group VA element, a selenide of a Group VIA element, and a combination thereof.

Desirably, the melting point of the selected added co-catalyst is lower than the thermal self-catalysis temperature of the benzoxazine employed.

Crystalline or amorphous forms of elemental sulfur may be used as a co-catalyst. Elemental sulfur is nominally described as a $S_8$ ring, although other polymers and oligomers are known. Various allotropic forms of elemental selenium may be used. Nominally, selenium sulfide refers to many different compounds of sulfur and selenium, but is generally given by the formula $SeS_2$. Phosphorus sesquisulfide, phosphorus pentasulfide, and tetrasulfur tetranitride can be used.

Other suitable co-catalysts are salts of an organometallic complex cation. Such compounds include cations that have at least one carbon atom bonded to a transition metal atom.

In certain embodiments of polymerizable compositions of the disclosure, the organometallic complex salt of the polymerizable compositions of the present disclosure is represented by the following formula:

$$[L^1)_y(L^2)_zM]^{+q}X \qquad (XX)$$

wherein in Formula (XX):
Polymerizable compositions of the disclosure include one or more curatives. Such curatives are selected from the group of a thiol compound, an amine compound, and a combination thereof. In certain embodiments, at least one of the thiol compound and the amine compound is polyfunctional. Such curatives can function as reactive diluents.

Useful such compounds have at least one nucleophilic functional group that ring-opens the benzoxazine. Such compounds are of the generally formula:

$R^{30}\text{—(ZH)}_p$ \qquad (XII)

wherein,
$R^{30}$ is a (hetero)hydrocarbyl group;
each Z is independently —S— or —$NR^{31}$, where $R^{31}$ is H or a hydrocarbyl group, including aryl and alkyl; and
p is 1 to 6 (in certain embodiments, p is at least 2).

As mentioned above, the polymerization of benzoxazine monomers to a polymer is believed to be an ionic ring opening polymerization which converts the oxazine ring to another structure, e.g., linear polymer or larger heterocyclic rings. It is thought that a chain transfer step(s) limits the molecular weight of the resulting polymer and causes some branching. The ring-opening reaction may be represented by the following Scheme II for reaction of a benzoxazine based on bisphenol A with a curative of formula $R^{10}\text{—(ZH)}_2$ to form a polymeric material:

wherein
each $R^1$ is independently H or an alkyl group, and is the residue of an aliphatic aldehyde,
each $R^{Aryl}$ is independently the residue of an aryl amine having a boiling point greater than 200° C.;
each $R^{30}$ is independently a (hetero)hydrocarbyl group;
Z is a —S— or —$NR^{11}$, wherein each $R^{11}$ is H or a hydrocarbyl group, including aryl and alkyl p is 1 to 6, or 2 to 6; and
q is the number of repeat units and is at least 1 (in certain embodiments, q is at least 2).

Although the curative illustrated in Scheme II only has two —ZH groups, other curatives can have more than two —ZH groups. Thus, after reacting with two benzoxazine groups, such curatives can have additional —ZH groups available for further reactions with additional benzoxazine groups. Further, in embodiments where the starting benzoxazine was prepared with a polyamine, $R^{Aryl}$ groups may be connected to additional benzoxazine groups. Note further that as the composition comprises at least one polyfunctional thiol compound or amine compound, polymeric reaction products result.

In these embodiments there is an excess of benzoxazine, as an unreacted benzoxazine will homopolymerize in the presence of the catalyst to form a coextensive mixture or polymer network of benzoxazine adducts with the curative of Formula (XII) and poly(benzoxazines). In such embodiments, the molar amounts ratio of benzoxazine groups to the sum of amine and/or thiol "Z" groups from the compound $R^{30}\text{—(ZH)}_p$, is 3:2 to 100:1, or in certain embodiments 4:1 to 50:1.

With reference to the curative of Formula (XII), $R^{30}(ZH)_p$, the benzoxazine ring may be ring-opened by an amine compound. Useful amine compounds correspond to primary and secondary amines of the formula:

$R^{30}(NHR^{11})_p$ \qquad (XIII)

wherein, in Formula (XIII), $R^{30}$, $R^{11}$, and p are as defined above for Formula (XII). Such compounds include primary and secondary (hetero)hydrocarbyl monoamines and polyamines. The amino groups may be on a primary or secondary carbon. In the compounds of Formula (VIII), the $R^{10}$ may be (hetero)hydrocarbyl group that has a valence of p, and is the residue of a mono-, di- or higher amine having at least one primary amine group. The $R^{30}$ can be an alkyl, a cycloalkyl or aryl, and p is 1 to 4, or 2 to 4. In certain embodiments, the $R^{30}$ is selected from mono- and polyvalent (hetero)hydrocarbyl (i.e., alkyl and aryl compounds having 1 to 30 carbon atoms, or alternatively (hetero)hydrocarbyl including heteroalkyl and heteroaryl having 1 to twenty heteroatoms of oxygen). Each $R^{11}$ is independently H or a hydrocarbyl group, including aryl and alkyl, and p is 1 to 6, or 2 to 6. It will be clear to one skilled in the art that the same amines used in the preparation of the benzoxazines will also be useful in the ring-opening reaction.

The benzoxazine ring may also be opened with thiols of the formula:

$$R^{30}-(SH)_p \quad (XIV)$$

wherein, in Formula (XIV), $R^{30}$ and p are as defined above for Formula (XIII). That is, in the compounds of Formula (XIV), p is 1 to 6, or 2 to 6, and $R^{30}$ includes a (hetero)hydrocarbyl group, including aliphatic and aromatic monothiols and polythiols. $R^{30}$ may optionally further include one or more functional groups including hydroxyl, acid, ester, cyano, urea, urethane and ether groups. The thiol groups may be on a primary or secondary carbon.

In some preferred embodiments, the thiol compounds of Formula (XIV) are of the formula:

$$R^{32}-[(CO_2)_x-R^{33}-SH]_y \quad (XV)$$

wherein in Formula (XV):
$R^{32}$ is an alkylene group, an aryl group, an oxyalkylene group, or combination thereof; $R^{33}$ is a divalent hydrocarbyl group;
x is 0 or 1; and
y is 1 to 6, preferably 2 to 6.

In certain embodiments, the compounds of Formulas (XV) to are those in which $R^{32}$ is an alkylene group.

Useful alkyl thiols include methyl, ethyl and butyl thiol. Other useful thiols include 2-mercaptoethanol, 3-mercapto-1,2-propanediol, 4-mercaptobutanol, mercaptoundecanol, 2-mercaptoethylamine, 2,3-dimercaptopropanol, 3-mercaptopropyltrimethoxysilane, mercaptoalkanoic acids and esters thereof including mercaptoproionic acid, 2-chloroethanethiol, 2-amino-3-mercaptopropionic acid, dodecyl mercaptan, thiophenol, 2-mercaptoethyl ether, and pentaerythritol tetrathioglycolate. Specific examples of useful polythiols include dimercaptodiethyl sulfide; 1,6-hexanedithiol; 1,8-dimercapto-3,6-dithiaoctane; propane-1,2,3-trithiol; 1,2-bis[(2-mercaptoethyl)thio]-3-mercaptopropane; tetrakis(7-mercapto-2,5-dithiaheptyl)methane; and trithiocyanuric acid.

Another useful class of polythiols includes those obtained by esterification of a polyol with a terminally thiol-substituted carboxylic acid (or derivative thereof such as esters or acyl halides) including α- or β-mercaptocarboxylic acids such as thioglycolic acid or β-mercaptopropionic acid or esters therof. Useful examples of compounds thus obtained include ethylene glycol bis(thioglycolate), pentaerythritol tetrakis(3-mercaptopropionate), ethylene glycol bis(3-mercaptopropionate), trimethylolpropane tris(thioglycolate), trimethylolpropane tris(3-mercaptopropionate), pentaerythritol tetrakis(thioglycolate) pentaerythritol tetrakis(3-mercaptopropionate), all of which are commercially available. A specific example of a polymeric polythiol is polypropylene ether glycol bis(3-mercaptopropionate) which is prepared from polypropylene-ether glycol (e.g., that available under the trade name PLURAXOL P201 from BASF Wyandotte Chemical Corp.) and 3-mercaptopropionic acid by esterification.

In some embodiments, useful thiols include those thiols derived from epoxy compounds. The polythiol may be derived from the reaction between $H_2S$ (or equivalent) and an epoxy resin having two or more functional groups and preferably having a molecular weight of less than 1000. For example, bifunctional epoxy resins, such as a bisphenol A epoxy resin and a bisphenol F epoxy resin, and novolak epoxy resins, such as a phenolic novolak epoxy resin and a cresol novolak epoxy resin, or amine epoxy resins, can be used. In addition, generally known polyfunctional epoxy resins, heterocycle-containing epoxy resins, and alicyclic epoxy resins can be used. These epoxy resins may be used alone or in combinations of two or more chemical types or molecular weight ranges.

A particularly useful polythiol is that derived from bisphenol-A diglycidyl ether, available as QX-11 from Japan Epoxy Resins, having a thiol equivalent weight of approximately 245 and the following general structure, where n is at least 1:

(XIV)

Useful soluble, high molecular weight thiols include polyethylene glycol di(2-mercaptoacetate), and those resins available under the trade names LP-3 (supplied by LP North America, Houston, Tex.) and PERMAPOL P3 (supplied by Products Research & Chemical Corp., Glendale, Calif.), and compounds such as the adduct of 2-mercaptoethylamine and caprolactam.

The compounds of Scheme I may be prepared by combining the benzoxazine compounds with a curative either neat or in a suitable solvent. Suitable solvents include those in which the reactants dissolve, preferably at room temperature, and that are nonreactive with the various components in the polymerizable composition. Examples of suitable solvents include butyl acetate, toluene, xylene, tetrahydrofuran, ethylene glycol dimethyl ether and the like. Heating is generally unnecessary as the thiol and amine-induced ring opening is exothermic.

Combinations of various curatives can be used if desired.

If used, a curative is present in an amount of at least 5 wt. %, and often as much as 60% of the benzoxazine equivalent.

Polymerizable compositions of the present disclosure may include a film-forming material, which can be in the form of monomers, oligomers, polymerizable pre-polymers, polymers, or a combination thereof. These materials, as the name suggests, enable the formation of benzoxazine-containing films that reduce the brittleness of typical benzoxazines. Such films are typically flexible and tacky over a desired temperature window in the sub-ambient to benzoxazine-cure temperature range. The film-former may be reactive or nonreactive with the benzoxazine, or any other components such as the catalyst, co-catalyst, curative, toughener, and the like.

In some embodiments the film-formers are materials, particularly oligomers or polymers, which form a homogenous mixture with the benzoxazine/catalyst mixtures at processing temperatures, preferably from sub-ambient to the processing of the polymerizable benzoxazine composition. Catalyst present in these films provides for excellent shelf life even when the films are stored at elevated temperatures.

Optionally, film formers can have reactive functional groups that react with a portion of the benzoxazine. The film-forming material may include a reactive film-forming material that includes one or more functional groups reactive with the benzoxazine, such as those selected from the group of a thiol, an amine, a benzoxazine, a formaldehyde, an aldehyde, and a combination thereof. The reactive film-forming material may include a compound that can react with, and be bonded to, the benzoxazine. The presence of one or more functional groups can afford increased processability options for said films: they can be processed above or below the reaction temperature of the reactive group to afford variable degree of tack, flexibility, and other desirable properties. Examples of such reactive film formers include, but are not limited to, amine-terminated butadiene-nitrile (ATBN), hydroxy-terminated butadiene-nitrile (HOTBN), carboxy-terminated butadiene-nitrile CTBN, amine-terminated poly(alkylene oxides) (such as those available under the trade names JEFFAMINE and VERSALINK) and related compounds.

In some embodiment the reactive film-formers may have different reactive groups in the backbone and termini. Examples of such materials include the end-functional butadiene-nitrile rubbers such as ATBN, which has unsaturation in its repeat unit and amine functional reactive groups on its ends. The amine functional groups may react with the benzoxazine by nucleophilic ring-opening (e.g., as described herein with respect to the curatives), and the unsaturation may react with the catalyst by vulcanization.

Examples of suitable nonreactive film-forming polymers for coating formulations include acrylic polymers (e.g., poly(methyl methacrylate-co-ethyl acrylate) and poly(methyl acrylate-co-acrylic acid)); polyurethanes (e.g., reaction products of aliphatic, cycloaliphatic or aromatic diisocyanates with polyester glycols or polyether glycols); polyolefins; polystyrene; copolymers of styrene with acrylate(s) (e.g., poly(styrene-co-butyl acrylate); polyesters, (e.g., polyethylene terephthalate, polyethylene terephthalate isophthalate, and polycaprolactone); polyamides, (e.g., polyhexamethylene adipamide); vinyl polymers, (e.g., poly(vinyl acetate/methyl acrylate) and poly(vinylidene chloride/vinyl acetate); polydienes, (e.g., poly(butadiene/styrene)); cellulosic polymer including cellulose ethers and cellulose esters, (e.g., ethyl cellulose and cellulose acetate/butyrate); polyimides; polysulfones; urethane-acrylate copolymers; and polyethers. Such polymers are available, for example, from commercial sources or may be prepared using methods and starting materials known in the art.

Combinations of various film-forming materials may be used if desired.

If used, film-forming material is present in an amount of at least 10 wt-%, and in certain embodiments, at least 25 wt-%, based on the total weight of the polymerizable composition. If used, film-forming material is present in an amount of no greater than 75 wt-%, and in certain embodiments, no greater than 50 wt-%, based on the total weight of the polymerizable composition.

Certain other optional additives may also be included, including, for example, tougheners, epoxy resin, and other reactive diluents. Such additives provide various functions (e.g., film formation). For example, a toughening agent may reduce brittleness and/or add strength to the composition after curing without interfering with curing. An epoxy resin may reduce the viscosity, lower $T_g$, and/or function as a carrier for a toughening agent.

It will be understood by one of skill in the art that one compound may form two or more different functions. For example, a compound may function as both a toughening agent and a curative.

In some embodiments, such additives will not react with the benzoxazine. In some embodiments, such additives may include reactive functional groups, particularly as end groups.

Examples of such reactive functional groups include, but are not limited to, amines, thiols, alcohols, epoxides, vinyls, and combinations thereof. Toughening agents are useful in polymerizable compositions of the present disclosure are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl ($C_1$-$C_4$) substituted methacrylates. Exemplary monovinyl aromatic hydrocarbons are styrene, alpha-methyl styrene, vinyltoluene, vinylxylene, ethylvinylbenzene, isopropylstyrene, chlorostyrene, dichlorostyrene, and ethylchlorostyrene. It is important that the graft copolymer contain no functional groups that would poison the catalyst.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of toughening agents useful in the invention includes elastomeric particles that have a glass transition temperature ($T_g$) below 25° C. before mixing with the other components of the composition. These elastomeric particles are polymerized from free radical polymerizable monomers and a copolymerizable polymeric stabilizer that is soluble in the benzoxazine. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, Pa.), those having a core including polybutadiene and a shell including poly(methyl methacrylate) (for example, those available under the trade names KANE ACE M511, M521, B11A, B22, B31, and M901 from Kaneka Corporation, Houston, Tex. and CLEARSTRENGTH C223 from ATOFINA, Philadelphia, Pa.), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HCl 101 (i.e., polytetramethylene oxide diamine) a 10,000 MW, primary amine-terminated, compound from 3M Co., St. Paul, Minn., and those available under the trade name JEFFAMINE from Huntsman Chemical Co., Houston, Tex.; functional acrylic rubbers including acrylic core/shell materials, such as those available under the trade names ACRYLOID KM330 and 334 from Rohm & Haas; and core/shell polymers, such as methacrylate-butadiene-styrene (MBS) copolymer wherein the core is crosslinked styrene/butadiene rubber and the shell is polymethylacrylate (e.g., that available under the trade names ACRYLOID KM653 and KM680; Rohm and Haas). Useful liquid poly-butadiene hydroxyl terminated resins include those available under the trade names LIQUIFLEX H by Petroflex of Wilmington, Del., and HT 45 by Sartomer of Exton, PN.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

It will be appreciated that some of the described natural and synthetic rubbers will have unsaturation in the chain that can be crosslinked by the catalyst. Thus, the catalyst will polymerize the benzoxazine, and concurrently vulcanize the rubber to for a coextensive network of poly(benzoxazine) and vulcanized rubber.

Various combinations of toughening agents can be used if desired.

If used, a toughening agent is present in a polymerizable composition in an amount of at least 3 wt-%, or at least 5 wt-%, based on the weight of the benzoxazine. If used, a toughening agent is present in a polymerizable composition in an amount of no greater than 35 wt-%, or no greater than 25 wt-%, based on the weight of the benzoxazine.

Other optional additives include epoxy resins. Such materials may function as a curative, a reactive diluent, or a co-reactant. The epoxy group does not react directly with the benzoxazine as do the amines or thiols of the curatives, but the phenolic group resulting from the ring opening of the benzoxazine may further react to ring-open the epoxy groups.

Polyepoxy compounds which can be utilized in the compositions of the disclosure include both aliphatic and aromatic polyepoxides. In certain embodiments, glycidyl aliphatic epoxies are preferred. The aromatic polyepoxides are compounds containing at least one aromatic ring structure, e.g., a benzene ring, and more than one epoxy group. Preferred aromatic polyepoxides include the polyglycidyl ethers of polyhydric phenols (e.g., bisphenol A derivative resins, epoxy cresol-novolac resins, bisphenol F derivative resins, epoxy phenol-novolac resins) and the glycidyl esters of aromatic carboxylic acids. The most preferred aromatic polyepoxides are the polyglycidyl ethers of polyhydric phenols.

Representative examples of aliphatic polyepoxides which can be utilized in the composition of the disclosure include 3',4'-epoxycyclohexylmethyl-3,4-epoxycyclohexanecarboxylate, 3,4-epoxycyclohexyloxirane, bis(3,4-epoxycyclohexylmethyl)adipate, the diglycidyl ester of linoleic dimer acid, 1,4-bis(2,3-epoxypropoxy)butane, 4-(1,2-epoxyethyl)-1,2-epoxycyclohexane, 2,2-bis(3,4-epoxycyclohexyl)propane, polyglycidyl ethers of aliphatic polyols such as glycerol or hydrogenated 4,4'-dihydroxydiphenyldimethylmethane, and mixtures thereof. Preferred such polyepoxides do not include cycloaliphatic groups.

Representative examples of aromatic polyepoxides, which can be utilized in the composition of the disclosure, include glycidyl esters of aromatic carboxylic acids, e.g., phthalic acid diglycidyl ester, isophthalic acid diglycidyl ester, trimellitic acid triglycidyl ester, and pyromellitic acid tetraglycidyl ester, and mixtures thereof; N-glycidylaminobenzenes, e.g., N,N-diglycidylbenzeneamine, bis(N,N-diglycidyl-4-aminophenyl)methane, 1,3-bis(N,N-diglycidylamino)benzene, and N,N-diglycidyl-4-glycidyloxybenzeneamine, and mixtures thereof; and the polyglycidyl derivatives of polyhydric phenols, e.g., 2,2-bis-(4-(2,3-epoxypropoxy)phenylpropane, the polyglycidyl ethers of polyhydric phenols such as tetrakis(4-hydroxyphenyl)ethane, pyrocatechol, resorcinol, hydroquinone, 4,4'-dihydroxydiphenyl methane, 4,4'-dihydroxydiphenyl dimethyl methane, 4,4'-dihydroxy-3,3'-dimethyldiphenyl methane, 4,4'-dihydroxydiphenyl methyl methane, 4,4'-dihydroxydiphenyl cyclohexane, 4,4'-dihydroxy-3,31-dimethyldiphenyl propane, 4,4'-dihydroxydiphenyl sulfone, and tris-(4-hydroxyphenyl)methane, polyglycidyl ethers of novolacs (reaction products of monohydric or polyhydric phenols with aldehydes in the presence of acid catalysts), and the derivatives described in U.S. Pat. No. 3,018,262 (Schroeder) and U.S. Pat. No. 3,298,998 (McConnell et al.), as well as the derivatives described in the Handbook of Epoxy Resins by Lee and Neville, McGraw-Hill Book Co., New York (1967), and mixtures thereof.

An exemplary class of polyepoxy compounds is polyglycidyl ethers of polyhydric alcohol, particularly polyphenols. The glycidyl epoxy compounds are generally more reactive toward amines than cycloaliphatic epoxy compounds. In some embodiments, the epoxy compound generally has an epoxy equivalent weight (EW) of 170 to 4,000, or 170 to 1,000. The epoxide equivalent weight (EW) is defined as the weight in grams of the epoxy functional compound that contains one gram equivalent of epoxy (oxirane) functional groups.

If used, an epoxy resin is present in a polymerizable composition in an amount of at least 5 wt-%, or at least 3 wt-%, based on the weight of the benzoxazine. If used, a toughening agent is useful in a polymerizable composition in an amount of no greater than 35-wt-%, or no greater than 25 wt-%, based on the weight of the benzoxazine.

Other optional additives, or adjuvants, may be added to the compositions as desired. Examples of such other optional additives include as colorants, abrasive granules, anti-oxidant stabilizers, thermal degradation stabilizers, light stabilizers, conductive particles, tackifiers, flow agents, bodying agents, flatting agents, inert fillers, binders, blowing agents, fungicides, bactericides, surfactants, plasticizers, rubber tougheners, and other additives known to those skilled in the art. Such additives are typically substantially unreactive, such as fillers, both inorganic and organic. These adjuvants, if present, or other optional additives, are added in an amount effective for their intended purpose.

The choice and amounts of optional components depend on the needs of the specific application. For example, for a structural/semi-structural benzoxazine adhesive, the polymerizable composition could contain silica fillers, glass bubbles, and tougheners. These adjuvants add toughness to and reduce the density of the polymerized composition. For a protective coating, such as an abrasion resistant coating, which is generally hard, requires a significant portion of the formulation to be a hard resin that includes generally short chain lengths and high functionality. Coatings undergoing some flex require toughness which can be obtained by using the above-mentioned additive to increase toughness and increase flexibility. Clear coatings require the cured resins to have little to no phase separation. This is obtained by controlling the compatibility of the resins or controlling phase separation by cure rate.

Reaction conditions for curing the composition depend on the reactants and amounts used and can be determined by those skilled in the art. The curable compositions are made by mixing in any order the benzoxazine compound and the alkylating agent described above. Generally, the composition is then heated to a temperature between about 50 and 200° C., preferably between about 130-180° C., for a time of about 1-120 minutes.

Suitable sources of heat to cure the compositions of the invention include induction heating coils, ovens, hot plates, heat guns, infrared sources including lasers, microwave sources. Suitable sources of light and radiation include ultraviolet light sources, visible light sources, and electron beam sources.

Solvents can be used to assist in dissolution of the acrylic (co)polymer in the benzoxazine monomers, and also as a processing aid. It may be advantageous to prepare a concentrated solution of the alkylating agent in a small amount of solvent to simplify the preparation of the polymerizable composition. Useful solvents are lactones, such as gamma-butyrolactone, gamma-valerolactone; and epsilon-caprolactone; ketones such as acetone, methyl ethyl ketone, methyl isobutyl ketone, cyclopentanone and cyclohexanone; sulfones, such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methyl sulfonyl)ethanol, 2,2'-sulfonyldiethanol; sulfoxides, such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as methylene chloride, nitromethane, acetonitrile, glycol sulfite and 1,2-dimethoxyethane (glyme).

Compositions of this invention are useful for coatings, foams, shaped articles, adhesives (including structural and semistructural adhesives), magnetic media, filled or reinforced composites, coated abrasives, caulking and sealing compounds, casting and molding compounds, potting and encapsulating compounds, impregnating and coating compounds, conductive adhesives for electronics, protective coatings for electronics, and other applications that are known to those skilled in the art. When uncured or partially cured, the benzoxazine compositions exhibit pressure-sensitive adhesive properties, including tack. In some embodiments, the present disclosure provides a coated article comprising a substrate, having a cured coating of the benzoxazine thereon.

To prepare a structural/semi-structural benzoxazine adhesive, the curable composition could contain additional adjuvants such as silica fillers, glass bubbles and tougheners. These adjuvants add toughness to and reduce the density of the cured composition.

To prepare protective coatings, the choice of materials depends on the needs of the specific application. Abrasion resistant coatings are generally hard and require a significant portion of the formulation to be a hard resin, which are generally short chain length and have high functionality. Coatings undergoing some flex require toughness which can be obtained by lowering the crosslink density of the cure formulation. Clear coatings require the cured resins to have little to no phase separation. This is obtained by controlling the compatibility of the resins or controlling phase separation by cure rate. Adjuvants could be added to these coating formulations in an amount effective for their intended use.

The composition may be coated onto substrates at useful thicknesses ranging from 25-500 micrometers or more. Coating can be accomplished by any conventional means such as roller, dip, knife, or extrusion coating. Solutions of the curable composition may be used to facilitate coating. Stable thicknesses are necessary to maintain the desired coating thickness prior to crosslinking of the composition to form the crosslinked composition.

Useful substrates can be of any nature and composition, and can be inorganic or organic. Representative examples of useful substrates include ceramics, siliceous substrates including glass, metal, natural and man-made stone, woven and nonwoven articles, polymeric materials, including thermoplastic and thermosets, (such as polymethyl (meth)acrylate), polycarbonate, polystyrene, styrene copolymers, such as styrene acrylonitrile copolymers, polyesters, polyethylene terephthalate), silicones, paints (such as those based on acrylic resins), powder coatings (such as polyurethane or hybrid powder coatings), and wood and composites of the foregoing materials.

The instant disclosure further provides a pressure-sensitive adhesive which comprises a coating of the uncured or partially cured benzoxazine composition on a suitable substrate, such as an adhesive tape backing. A preferred method of preparing a pressure-sensitive adhesive article comprises partially curing the novel composition to a useful coating viscosity, coating the partially crosslinked composition onto a substrate (such as a tape backing) and further curing the composition. Useful coating viscosities are generally in the range of 500 to 10,000 cps.

EXAMPLES

Test Methods
Differential Scanning Calorimetry of Cure (DSC Analysis)

The thermal properties of a composition during curing were determined by placing an amount of the composition in an open aluminum pan in a Differential Scanning calorimeter (DSC) and heating from 25° C. to 300° C. or 330° C. at a heating rate of 10° C./min. The DSC instrument was from TA Instruments, New Castle, Del., was designated as "TA", and the DSC from Seiko Instruments USA, Inc., Torrance, Calif. was designated as "Seiko". The peak cure temperature in ° C. ("Peak"), the approximate cure onset temperature in ° C. ("Onset"), and the total energy released ("Energy") in Joules/gram (J/g) during curing of the composition from the DSC trace were reported.

Nuclear Magnetic Resonance (NMR Analysis)

Nuclear magnetic resonance spectra ($^{13}$C NMR, $^1$HNMR, HSQC and HMBC NMR) were determined using an NMR spectrometer (Varian Inova 600 MHz NMR spectrometer equipped with an inverse probe head with the NMR sample held at 25° C.). The NMR provided information that was an indication of the curing of the polymer, and an indication of whether or not the catalyst was incorporated into the polymer chain.

Solid State Nuclear Magnetic Resonance (Solid State NMR Analysis)

Samples were submerged in liquid nitrogen and ground with a mortar and pestle. The samples were packed in to Varian 4 mm rotors. All data was collected on a Varian NMRS 400 MHz solid-state NMR spectrometer equipped with a Varian 4 mm Magic Angle Spinning (MAS) probe. The sample was held at 25° C. during the experiment. MAS speeds of 8 kHz or 10 kHz were used. Proton spectra were collected using a single 90° pulse of 2.5 milliseconds (ms). $^{13}$C CP/MAS spectra were collected using a tangent cross polarization experiment with a 2.5 ms $^1$H pulse preceding the cross polarization step. The $^1$H power was set to 62.5 kHz and the $^{13}$C power was optimized at a power level equivalent to the first spinning sideband below 62.5 kHz. The data was apodizied with a Gaussian function of 50 Hz, Fourier Transformed, phased, and baseline corrected using ACD software. Homonuclear decoupled $^1$H spectra were collected using the DUMBO pulse sequence. This experiment narrows the otherwise very broad lines such that aromatic and aliphatic peaks can be detected. The DUMBO sequence was used as a homonuclear decoupling step in a $^{13}$C{$^1$H} heteronuclear correlation experiment (HETCOR). These result in a 2D data where the indirect (proton) dimension has been narrowed by the DUMBO sequence. This couple with Lee-Goldburg (LG) cross polarization limits the $^1$H spin diffusion and results in the resolution of aromatic an aliphatic resonances with the $^{13}$C chemical shift. The aromatic spinning sidebands were easily detected.

Headspace Mass Spectroscopy
Sample Prep:

Approximately 25 mg of sample were weighed into a 20 mL headspace vial. The vial was sealed with an aluminum crimp cap with a poly(tetrafluoroethylene) lined silicone septum. The samples were heated at 220° C. for 15 minutes prior to the analysis of the headspace.

GC/MS Conditions:

GC: Agilent 6890 Plus GC System; MSD: Agilent 5973 Network Mass Selective Detector; Column: Agilent J&W DB-5MS, 30 meter by 0.32 mm by 1 micrometer; 2.0 mL/min Constant Flow; 180° C. Injector Temp; Oven: 40° C. hold 1 min, 15° C./min to 320° C. hold 5.33 min; Split Injection (10:1); MS EI Full Scan 15-550 amu.

Headspace Conditions:

HS: Agilent G1888 Network Headspace Sampler; Oven Temp 220° C.; Loop Temp 230° C.; Transfer Line Temp 240° C.; Vial Equilibration Time 15 min; Inject Time 1 min; Vial Pressurization Time 1 min.

Method Conditions:

Headspace instrument: Agilent G1888 Headspace Sampler
Sample oven temperature: 220° C.
Loop temperature: 230° C.
Transfer line temperature: 240° C.
Vial equilibration time: 15 min
Inject time: 1 min
Vial pressurization time: 1 min
GC cycle time: 35 min
GC Instrument: Agilent 6890 Plus GC, MSD: Agilent 5973 Mass Selective Detector
Column: J&W DB-5-MS, 30 m×0.32 mm
Column temperature: 40° C. hold 1 min, increase to 320° C. at a linear rate of 15° C./min; hold for 5.33 min Carrier: 2.0 mL/min, constant flow
Injection: Split mode (10/1)
Detection: Electron impact (EI) mode, 70 eV, m/z 15-550

Thermogravimetric Analysis (TGA)

The thermal stability of the amine cured benzoxazine compositions was determined using thermogravimetric analysis (TGA). A 5-10 mg sample of the composition was placed on platinum pans in an thermogravimetric analyzer (TA Q500 THERMOGRAVIMETRIC ANALYZER) under an air purge of 60 ml per minute, and heated from ambient temperature to 500° C. with a constant ramp rate of 10° C. per minute.

The activation energy of the initial decomposition events were investigated the Ozawa/Fylnn/Wall method as described in ASTM standard E1641. Aliquots of 5-10 mg of the material were placed on platinum pans in an thermogravimetric analyzer (TA Q500 THERMOGRAVIMETRIC ANALYZER) under an air purge of 60 ml per minute. Heating rates of 20, 10, 5, and 2° C. per minute were employed to record the weight loss of each sample from 25° C. to 500° C.

Unless stated otherwise, materials used in the examples were available from chemical suppliers such as Sigma-Aldrich Corp., St. Louis, Mo.

TABLE 1

MATERIALS

| Designation | Description and Source |
| --- | --- |
| BZ-1 | A benzoxazine monomer obtained from Huntsman Chemical, Houston, TX, under the trade designation "ARALDITE MX 35600" |
| BZ-2 | p-D benzoxazine (phenyl ether of methylene dianiline benzoxazine obtained from Shikoku, Japan. |
| BZ-3 | Ph-BAPP Benzoxazine, prepared as described in PE-1 |
| AM-1 | m-xylene diamine, obtained from Mitsubishi Gas Chemical Co., Inc., Tokyo, Japan, under the trade designation "MXDA" |
| AM-2 | 1,3-benzenedimethanamine, reaction product with epichlorohydrin (according to the supplier's description), obtained from Mitsubishi Gas Chemical Co., Ltd., Tokyo, Japan, under the trade designation "GASKAMINE 328" |

TABLE 1-continued

MATERIALS

| Designation | Description and Source |
|---|---|
| AM-3 | Benzylamine, obtained from Sigma-Aldrich Corp., Milwaukee, WI |

Preparatory Example 1 (PE-1): Ph-BAPP Benzoxazine (BZ-3)

BZ-3

Ph-BAPP benzoxazine (BZ-3) was prepared as follows: A 500 mL flask with magnetic stir bar was loaded with 2,2-bis[4-(4-aminophenoxy)phenyl]propane (10.26 g, 25.00 mmol), phenol (2.35 g, 50 mmol), paraformaldehyde (3.08, 100 mmol), and xylenes (62.5 mL). The flask was fitted with a water-cooled condenser and the solution was heated to 140° C. for three hours. After that time, the reaction was cooled to 25° C. and the reaction solution was poured in to 750 mL of cold Hexanes. The colorless precipitate was isolated via vacuum filtration and dissolved in chloroform (100 mL). The chloroform solution was sequentially washed with 1 M NaOH (3×50 mL), water (50 mL) and saturated aqueous sodium chloride (50 mL). After drying the solution over $Na_2SO_4$, all volatiles were removed under vacuum resulting in a light yellow solid in 70.8% yield. Molecular structure was confirmed using $^1H$ and $^{13}C$ NMR.

Comparative Example 1 (CE-1): Reaction of AM-1 with BZ-1

0.34 gram (0.01 mol of Active Hydrogen Equivalent) of AM-1 was admixed with 2.31 grams (0.01 mol of benzoxazine) of BZ-1 and stirred for several minutes at room temperature until a uniform paste was obtained.

Example 1 (EX-1)

0.34 grams (0.01 mol of Active Hydrogen Equivalent) of AM-1 were admixed with 2.17 grams (0.01 mol of benzoxazine) of BZ-2 and stirred for several minutes at room temperature until a uniform paste was obtained.

Figure 1:
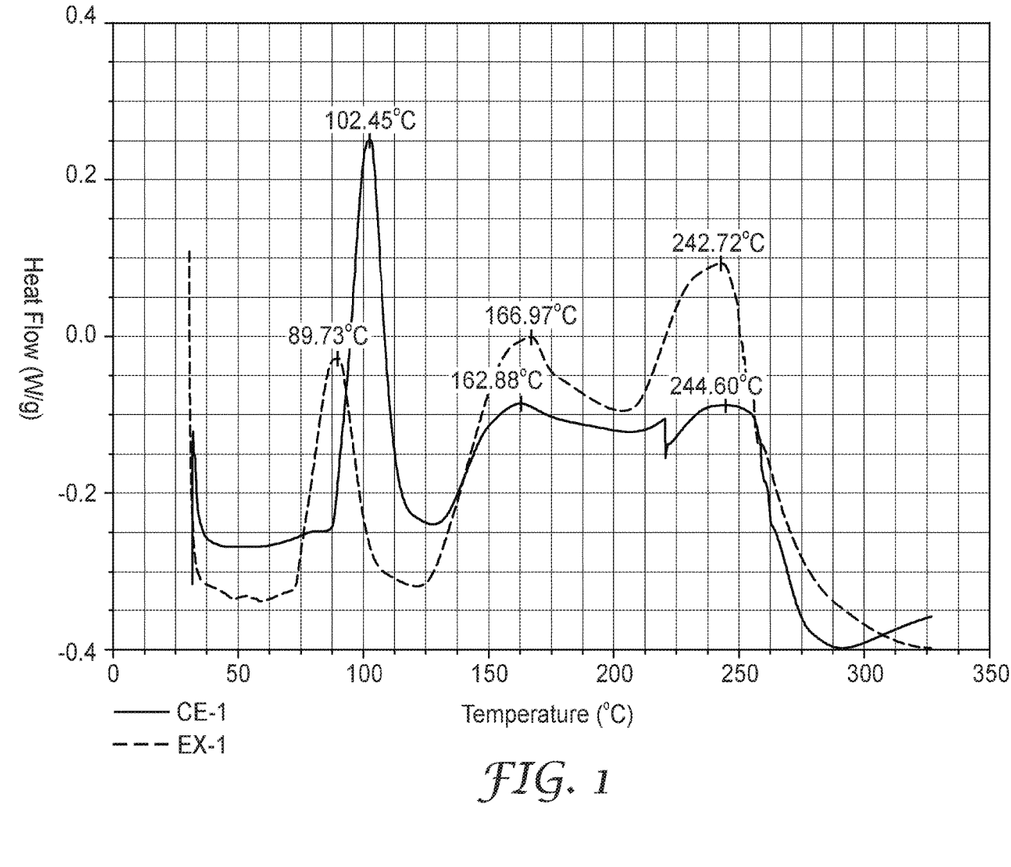
FIG. 1 is a DSC plot of Ex. 1 and Comparative Example 1

Aliquots of CE-1 and EX-1, were subjected to DSC analysis. Each showed a profile with 3-exothermic peaks as shown in FIG. 1. A noticeable difference in the cure profiles of the two samples was observed as a sharp endotherm for CE-1 near 220° C., that is absent for EX-1.

TGA

Comparative Example 2 (CE-2)

An aliquot of sample of CE-1, above, was heated at 180° C. for 1 hour. To investigate the weight loss during post-cure at temperatures above 200° C., an aliquot of that mixture was used for TGA at 10° C./minute heating rate. The results of that scan were as summarized in Table 1, below.

Example 2 (Ex-2)

0.34 grams (0.01 mol of Active Hydrogen Equivalent) of AM-1 were admixed with 2.17 grams (0.01 mol of benzoxazine) of BZ-2 and stirred for several minutes at room temperature until a uniform paste was obtained. The sample was then cured in an air-circulating oven at 180° C. for two hours. To investigate the weight loss during post-cure at temperatures above 200° C., an aliquot of that mixture was used for TGA at 10° C./minute heating rate. The results of that scan were as summarized in Table 1.

Example 3 (Ex-3)

0.55 grams (0.01 mol of Active Hydrogen Equivalent) of AM-2 were admixed with 2.17 grams (0.01 mol of benzoxazine) of BZ-2 and stirred for several minutes at room temperature until a uniform paste was obtained. The sample was then cured in an air-circulating oven at 180° C. for two hours. To investigate the weight loss during post-cure at temperatures above 200° C., an aliquot of that mixture was used for TGA at 10° C./minute heating rate. The results of that scan were as summarized in Table 1, below.

Example 4 (Ex-4)

0.34 grams (0.01 mol of Active Hydrogen Equivalent) of AM-1 were admixed with 3.23 grams (0.01 mol of benzoxazine) of BZ-3 and stirred for several minutes at room temperature until a uniform paste was obtained. The sample was then cured in an air-circulating oven at 180° C. for one hour. To investigate the weight loss during post-cure at temperatures above 200° C., an aliquot of that mixture was used for TGA at 10° C./minute heating rate. The results of that scan were as summarized in Table 1, below.

TABLE 1

5% and 10% Weight loss temperatures of CE-2, EX-2, EX-3 and EX-4

| EXAMPLE | 5% Weight loss Temperature (° C.) | 10% Weight loss Temperature (° C.) |
|---|---|---|
| CE-2 | 279.44 | 309.45 |
| EX-2 | 290.53 | 431.57 |
| EX-3 | 316.49 | 430.99 |
| EX-4 | 323.22 | 428.70 |

Comparative Example 3 (CE-3)

4.62 grams (0.02 mol of benzoxazine Equivalents) of BZ-1 were heated to 100° C. admixed with 0.68 grams (0.02 mol of Active Hydrogen Equivalent) of AM-1 in a 20 mL glass vial. An aliquot of the mixture was cured at 180° C. for 1 hour in an air-circulating oven.

Comparative Example 3 (CE-4)

2.31 grams (0.01 mol of benzoxazine) of BZ-1 were heated to 100° C. admixed with 0.55 grams (0.01 mol of Active Hydrogen Equivalent) of AM-2 while stirring. An aliquot was cured at 180° C. for 1 hour in an air-circulating oven.

Example 5 (Ex-5)

4.34 grams (0.02 mol of benzoxazine Equivalents) of BZ-2 were heated to 100° C. admixed with 0.68 grams (0.02 mol of Active Hydrogen Equivalent) of AM-1 in a 20 mL glass vial. An aliquot of the mixture was heated at 180° C. for 1 hour in an air-circulating oven.

Example 6 (Ex-6)

3.24 grams (0.01 mol of benzoxazine Equivalents) of BZ-3 were heated to 100° C. admixed with 0.34 grams (0.01 mol of Active Hydrogen Equivalent) of AM-1 in a 20 mL glass vial. An aliquot of the mixture was heated at 180° C. for 1 hour in an air-circulating oven.

Figure 2:
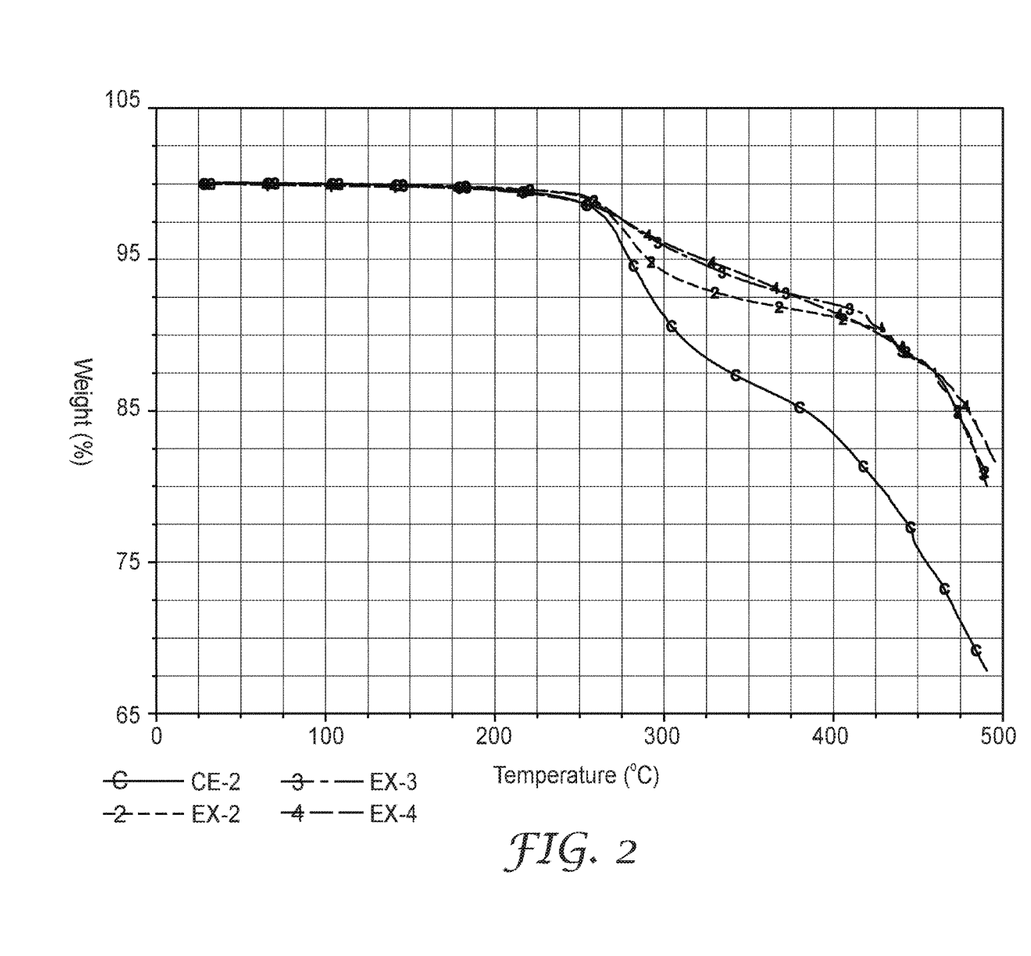
FIG. 2 is a TGA plot of Examples 2-4 and Comparative Example 2

Samples of CE-3, CE-4, EX-3, EX-5 and EX-6 were analyzed via Head Space Mass Spectroscopy (HSMS) and the results were as summarized in Table 2, below. THe DSC plot is shown in FIG. 2. The HSMS results of Table 2 confirm those observed in the TGA analysis above: replacing benzoxazine synthesized from lower boiling fragments like aniline with heavier methylene dianiline and phenol of EX-3, EX-5, and EX-6 dramatically reduces the amount of volatiles observed in HSMS and via TGA. Both of these observations confirmed that the benzoxazines of the present disclosure exhibited improved thermal stability while reducing the volume of volatiles produced at temperatures 180° C. and higher.

Hydrogen Equivalent) of AM-3 in a glass flask and stirred at room temperature until uniform. The mixture was then placed into an oven at 110° C. for 30 minutes. Aliquots were removed for NMR analysis at 5 minute, 15 minute and 30 minute intervals. NMR analysis (HSQC and HMBC) provided no detection of aminal products. NMR spectra were consistent with formation of imine products.

Example 8 (EX-8)

The reaction mixture of EX-7 was heated at 150° C. for an additional hour, producing a transparent hard glassy polymer, deep orange in color. An aliquot of this material was ground into a fine powder using mortar and pestle. 10 mg of this powder eventually dissolved in 2 mL of dmso-d6 after 24 hours at 100° C., for NMR analysis (HSQC).

Remarkably, after an hour at the temperature of the second polymerization exotherm, the reaction mixture of EX-8 remained soluble (though barely so).

Careful examination of the NMR spectra revealed disappearance of both benzoxazine monomers, the original BZ-2 and the benzylamine benzoxazine that formed in-situ at lower temperatures. Also vanishing were the Mannich bases that were replaced by various ortho- and para-substituted phenol structures, such as N-hydroxybenzyl anilinium and the "classical" N,N' dibenzylphenol amines. Also noted was the absence of any benzylanilinium rearrangement products that would manifest themselves as o-,o'- and o-,p'-methylene bridges with contours between the 30 ppm to 40 ppm carbon region.

Solid state NMR ($^{13}C\{^1H\}$ Dumbo-hetcor Solid State NMR) was also performed on the sample of EX-8 according to the procedure described in the Test Methods section. The 2-D NMR from that experiment detected the presence of contours in the aliphatic proton/40 ppm-60 ppm carbon region, and confirmed the absence of any carbons in the 30 ppm to 40 ppm region that would correspond to the formation of the methylene bridged phenolics.

TABLE 2

Summary of Significant Species Detected in HS-MS for Samples Cured at 180° C.

| | CE-3 AM-1/BZ-1 180° C., 25.8 mg | | EX-5 AM-1/BZ-2 180° C., 25.6 mg | | EX-6 AM-1/BZ-3 180° C., 25.3 mg | | CE-4 AM-2/BZ-1 180° C., 25.6 mg | | EX-3 AM-2/BZ-2 180° C., 25.1 mg | |
|---|---|---|---|---|---|---|---|---|---|---|
| | Peak Area | Area % | Peak Area | Area % | Peak Area | Area % | Peak Area | Area % | Peak Area | Area % |
| Water | 2.10E+07 | 1.87 | 1.98E+07 | 24.92 | 1.90E+07 | 16.89 | — | — | — | — |
| Toluene | 5.17E+07 | 4.60 | 3.78E+07 | 47.57 | — | — | 2E+08 | 4.14 | 1.97E+08 | 28.59 |
| Aniline | 1.02E+09 | 90.73 | 9.69E+06 | 12.19 | — | — | 3.83E+09 | 92.88 | 8.31E+06 | 1.21 |
| N-Methyl aniline | 1.02E+07 | 0.91 | — | — | — | — | 3.54E+07 | 0.86 | — | — |
| Nitrosobenzene | 1.98E+07 | 1.76 | — | — | — | — | 4E+07 | 0.99 | — | — |
| Phenol | — | — | 3.54E+06 | 4.45 | 7.99E+07 | 71.11 | — | — | 2.62E+08 | 37.97 |
| Methyl Phenol (isomers) | — | — | 1.34E+06 | 1.70 | 8.59E+06 | 7.64 | — | — | 8.89E+07 | 12.89 |
| Hydroxy-benzaldehyde (isomers) | — | — | 1.05E+06 | 1.32 | 4.50E+06 | 3.99 | — | — | — | — |
| Total | 1.12E+09 | | 7.95E+07 | | 1.12E+08 | | 4.10E+09 | | 6.89E+08 | |

NMR

Example 7 (EX-7)

To 2.17 grams (0.01 mol of benzoxazine equivalent) of BZ-2 were added to 0.535 grams (0.01 mol of Active Example 9 (EX-9)

The reaction mixture of EX-8 was then heated at 220° C. for an additional two hours, producing a transparent hard glassy polymer, darker brown in color. Solid state NMR ($^{13}C\{^1H\}$ Dumbo-hetcor Solid State NMR) was performed on the sample of EX-9. The 2-D NMR from that experiment, was consistent with the lack of any structural features in the 40 ppm-60 ppm carbon region, and the emergence of the structures in the 30 ppm to 40 ppm region corresponding to the formation of the methylene bridged phenolics.

Decomposition Activation Energy

The activation energies ($E_a$) for decomposition of CE-3 and EX-6 were investigated using TGA at variable heating rates as described in ASTM standard E1641. Aliquots of CE-3 and EX-6 were placed on platinum pans in a thermogravimetric analyzer (TA Q500 THERMOGRAVIMETRIC ANALYZER) under an air purge of 60 ml per minute. Heating rates of 20, 10, 5, and 2° C. per minute were employed to record the weight loss of each sample from 25° C. to 500° C. Analysis was performed at 3, 4, 5, and 6% weight loss to interrogate the initial decomposition event in these samples. Table 3 summarize the results of the study. The $E_a$ of decomposition for EX-6 is consistently greater than for CE-6 demonstrating superior thermal stability of benzoxazines derived from higher boiling amines than aniline are more thermally stable.

TABLE 3

Summary of $E_a$ of decomposition for CE-3 and EX-6 at various percent weight losses.

| % Weight Loss | CE-3 $E_a$ (kJ/mole) | EX-6 $E_a$ (kJ/mole) |
| --- | --- | --- |
| 3.0 | 105.6 | 121.8 |
| 4.0 | 112.1 | 137.0 |
| 5.0 | 122.8 | 153.7 |
| 6.0 | 131.8 | 209.4 |

What is claimed is:

1. A curable composition comprising a curable benzoxazine of the formula:

where
each $R^1$ is an alkyl or H;
each $R^2$ is an H, an alkyl, an aryl or a benzoxazine group;
y is 1 to 4
$R^{aryl}$ is derived from an aryl amine having a boiling point greater than 200° C.;
N-Bz represents a nitrogen-linked benzoxazine group, and
z is 0 to 3; and
a curative selected from the group of a thiol compounds, amine compounds, and a combination thereof.

2. The curable composition of claim 1 wherein the benzoxazine is derived from bisphenol-A.

3. The curable composition of claim 1 wherein $R^{aryl}$ is derived from an aryl amine having a boiling point greater than 210° C.

4. The curable composition of claim 1 wherein $R^{aryl}$ is derived from an aryl diamine and z is 1.

5. The curable composition of claim 1 wherein $R^{aryl}$ is selected from phenyl, napthyl, anthracenyl and biphenyl, each optionally substituted with one or more alkyl or aryl groups.

6. The curable composition of claim 1, wherein z is 0 or 1.

7. The curable composition of claim 1 derived from a phenol having a b.p.>200° C.

8. The curable composition of claim 1 further comprising a polyfunctional curative.

9. The curable composition of claim 1 further comprising a toughening agent.

10. The curable composition of claim 9, wherein said toughening agent is present at between about 3% and 35% by weight relative to the benzoxazine.

11. The curable composition of claim 1, further comprising a co-catalyst.

12. The curable composition of claim 11 wherein the co-catalyst is an acid catalyst.

13. The curable composition of claim 12 wherein the acid catalyst is a blocked acid catalyst.

14. The curable composition of claim 13 wherein the blocked acid catalyst is a tosylate.

15. The curable composition of claim 1 wherein the thiol curative is a polythiol.

16. The curable composition of claim 1 wherein the amine curative is a polyamine.

17. The curable composition of claim 1 wherein the curative is of the formula:

$$R^{30}-(ZH)_p$$

wherein,
$R^{30}$ is a (hetero)hydrocarbyl group;
each Z is independently —S— or $NR^{31}$, where $R^{31}$ is H or a hydrocarbyl group, including aryl and alkyl; and
p is 1 to 6.

18. The curable composition of claim 17 wherein p is 2 to 6.

19. The curable composition of claim 17 wherein the molar amounts ratio of benzoxazine groups to the "Z" groups, is 3:2 to 100:1.

20. The curable composition of claim 17 wherein the molar amounts ratio of benzoxazine groups to the "Z" groups, is 4:1 to 50:1.

21. The curable composition of claim 1 wherein the curative is present in an amount of at least 5 wt. %, to 60% of the benzoxazine equivalent.

22. The curable composition of claim 1 further comprising an epoxy resin.

23. The curable composition of claim 22 wherein the epoxy resin is used in amounts of 3 to 35 wt. % relative to the benzoxazine.

* * * * *